United States Patent [19]

Graham

[11] 4,435,191

[45] Mar. 6, 1984

[54] PROCESS FOR SEPARATING AGGRESSIVE GASES FROM GAS MIXTURES

[75] Inventor: Tommy E. Graham, Raleigh, N.C.

[73] Assignee: Monsanto Company, St. Louis, Mo.

[21] Appl. No.: 509,823

[22] Filed: Jun. 30, 1983

[51] Int. Cl.$^3$ .......................................... B01D 53/22
[52] U.S. Cl. ........................................ 55/16; 55/21; 55/69
[58] Field of Search ................ 55/16, 21, 68, 69, 70, 55/158

[56] References Cited

U.S. PATENT DOCUMENTS

| | | | |
|---|---|---|---|
| 3,534,528 | 10/1970 | Porter | 55/16 |
| 3,961,917 | 6/1976 | Benedict | 55/16 |
| 4,119,417 | 10/1978 | Heki | 55/16 |
| 4,130,403 | 12/1978 | Cooley | 55/16 |
| 4,180,553 | 12/1979 | Null | 55/16 |
| 4,198,213 | 4/1980 | Mannatt | 55/16 |
| 4,230,463 | 10/1980 | Henis | 55/16 |
| 4,239,506 | 12/1980 | Steigelmann | 55/16 |
| 4,255,591 | 3/1981 | Makin | 55/16 |
| 4,264,338 | 4/1981 | Null | 55/158 |

OTHER PUBLICATIONS

Ellig, "Concentration of Methane from Mixtures with Carbon Dioxide by Permeation Through Polymeric Films", Journal of Membrane Science, 6, No. 2, (Apr.) 1980, 259-263.

Primary Examiner—Ernest G. Therkorn
Attorney, Agent, or Firm—Robert L. Broad

[57] ABSTRACT

A process for separating large percentages of aggressive gases such as carbon dioxide from low temperature gas mixtures wherein the gas mixture is passed through a plurality of treatment zones in series. In each treatment zone the gas mixture is first compressed to a pressure such that the partial pressure of the carbon dioxide is not greater than the critical carbon dioxide partial pressure and the compressed gas mixture is then brought into contact with a membrane more permeable to carbon dioxide than other gases of the mixture such that carbon dioxide permeates the membrane to the other side thereof. The gas mixture is maintained in contact with the membrane a sufficient time to lower the partial pressure of the carbon dioxide in the non-permeated gas mixture to less than about 40 percent of said critical carbon dioxide partial pressure. The process is especially useful for separating carbon dioxide from methane and other gases.

9 Claims, 4 Drawing Figures

PROCESS FOR SEPARATING AGGRESSIVE GASES FROM GAS MIXTURES

BACKGROUND OF THE INVENTION

1. Field of the Invention

This invention relates to the separation of carbon dioxide and other aggressive gases from gas mixtures at low temperatures.

2. Prior Art

It is known to separate one gas from a mixture of gases by using a membrane more permeable to that one gas than the other gases of the mixture. The gas mixture is brought into contact with one side of the membrane and, under a pressure differential across the membrane, the one gas permeates to the other side of the membrane and is withdrawn. Frequently, these membranes are in the form of hollow fibers.

Often gas mixtures for which a membrane gas separation is desired may contain one or more species which may, under certain conditions, be detrimental to the operating characteristics of the membrane. Such species may adversely effect the membrane by solvation, plasticization, swelling, etc. The adverse effect may be a significant change in the permeability of the membrane for one or more of the gases of the mixture. In some cases, the permeability of the membrane changes for all gases in the mixture in such a manner that all of the gases pass rapidly through the membrane without any separation occurring. These adverse effects may be rapidly catastrophic or may be manifested as a gradual degradation of desired membrane properties over time. These adverse effects can usually be monitored by measuring permeability creep, i.e., the change in permeability, over a period of time. Depending on the particular membrane, adversely effecting species, such as ammonia, may be detrimental to the membrane even if the concentration, measured in terms of partial pressure, of the adversely effecting species is low. In other cases, such as the separation of an acid gas such as carbon dioxide or hydrogen sulfide from hydrocarbon gases such as methane, the acid gas is often present in substantial concentrations and is the predominant permeating species. In this regard, it is known that an acid gas, such as carbon dioxide, can under some conditions plasticize an otherwise rigid structure of a polymeric material such as polysulfone.

SUMMARY OF THE INVENTION

A process for separating aggressive gases such as carbon dioxide from low temperature gas mixtures wherein the gas mixture is passed through a plurality of treatment zones connected in series. In each treatment zone the gas mixture is first compressed to a pressure such that the partial pressure of the aggressive gas is not above the critical partial pressure of the gas. The compressed gas mixture is then brought into contact with a feed side of a membrane more permeable to the aggressive gas than the other gases of the mixture and is held in contact with the membrane a sufficient time to allow the aggressive gas to permeate the membrane sufficiently to lower the partial pressure of the aggressive gas to less than about 40 percent of the critical partial pressure. The gas mixture leaving the membrane of the last treatment zone will contain less than 20 percent of the aggressive gas and will be at a pressure of at least three times the pressure of the gas mixture in contact with the first membrane in the series.

DETAILED DESCRIPTION OF THE INVENTION

As used herein the following terms have the following meaning:

"Aggressive gas" is a gas which is capable of, at partial pressures above a critical partial pressure, swelling, solvating or otherwise changing a membrane sufficiently that the membrane exhibits a creep greater than 0.1.

"Critical partial pressure" is that partial pressure above which an aggressive gas will cause a given membrane to exhibit a creep of greater than 0.1.

"Creep" is the slope of the relationship of the logarithm of the permeability of a given membrane for a given aggressive gas as a function of the logarithm of time. A log-log plot of permeability versus time gives an essentially straight line which slopes downward to the right. In a mathematical sense, this slope will be negative, so that creep is a negative number. However, for the purposes herein, slope or creep will be considered as an absolute value, such that a creep of "less than 0.1" will represent a plotted line which is closer to horizontal than a line having an actual slope of $-0.1$ and a plotted creep "greater than 0.1" will be a line closer to vertical than a line having an actual slope of $-0.1$.

"Permeability" of a membrane for a particular gas through a membrane of thickness, "l", is the volume of gas, referred to standard temperature and pressure (STP), which passes through the membrane per unit of surface area of membrane, per unit of time, per unit of differential partial pressure of the gas. One method for expressing permeability is in cubic centimeters (STP) per square centimeter of membrane area per differential partial pressure of 1 centimeter of mercury across the membrane thickness [$cm^3(STP)/cm^2$-sec-cmHg]. Permeabilities are conventionally reported in gas separation units (GPU), which are $1 \times 10^6 \, cm^3(STP)/cm^2$-sec-Hg. To determine the creep of a membrane with respect to a given gas, the permeability of the membrane for that gas is measured at intervals over a length of time and the logarithm of measured permeabilities is plotted against the logarithm of time. The slope of the plotted line is the creep of the membrane.

Figure 1:
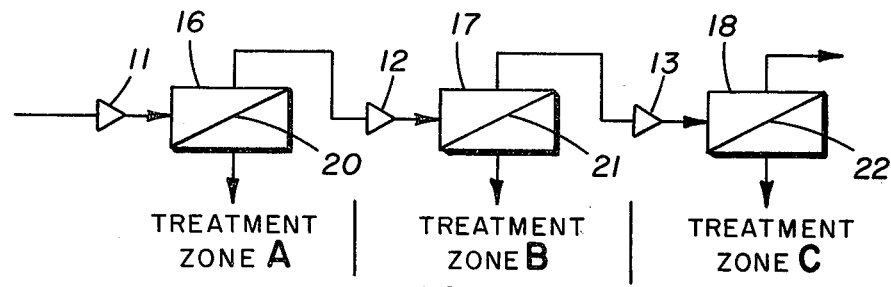
FIG. 1 is a schematic drawing of apparatus which may be used to carry the process of this invention.

Referring now in detail to the drawings, there is schematically shown in FIG. 1 apparatus for carrying out the process of this invention. The apparatus shown is made up of three treatment zones, A, B and C connected in series. It is necessary to use at least two treatment zones connected in series, with it being preferable to use at least three or more such zones, for the purpose of this invention. The purpose of the apparatus shown is to carry out a process wherein high percentages of aggressive gases such as those described herein can be separated from a gas mixture without heating the gas mixture to higher temperatures or using high partial pressures which would damage the membrane. In the treatment zones A–C, the gas mixture is first compressed by compressors 11, 12 and 13, respectively, to a pressure sufficiently high that the partial pressure of the aggressive gas in the mixture is at least 75 percent of the critical partial pressure of the aggressive gas. The compressed gas mixture is then fed into membrane separators 16, 17 and 18, respectively, having membranes 20, 21 and 22 which are more permeable to the aggressive gas to be separated from the mixture than the other gases of the mixture. The gas mixture is maintained in contact with the membrane a sufficient time to allow the aggressive gas to permeate the membrane to the other side thereof in an amount sufficient to lower the partial pressure of the aggressive gas in the non-permeated mixture to less than about 40 percent, preferably 30 percent, of the critical pressure of the aggressive gas. It should be understood that the compressors shown in FIG. 1 may be separate compressors or may be different stages of a single compressor.

Figure 3:
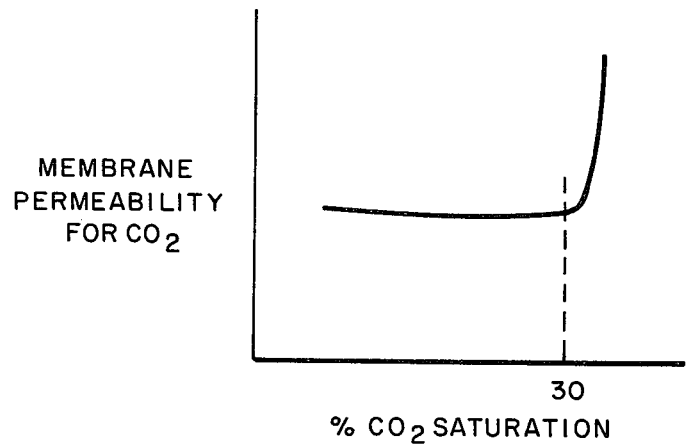
FIG. 3 is a graph showing the permeability of a polysulfone membrane for carbon dioxide plotted against partial pressure of carbon dioxide in contact with one side of the membrane.

FIG. 3 is a graph showing the permeability of a polysulfone polymeric membrane plotted against the partial pressure of carbon dioxide in contact with one side of the membrane. As the percent saturation or partial pressure of the carbon dioxide is increased, the permeability of the membrane for carbon dioxide remains essentially constant until the partial pressure exceeds about 30 percent of saturation, at which point the permeability of the membrane for carbon dioxide begins to increase dramatically. It is at this point that the membrane fails, since all of the gases of the mixture will now readily pass through the membrane. Thus, the critical partial pressure for carbon dioxide at a given temperature, with a polysulfone membrane, is about 30 percent of the carbon dioxide vapor pressure at this temperature.

Figure 2:
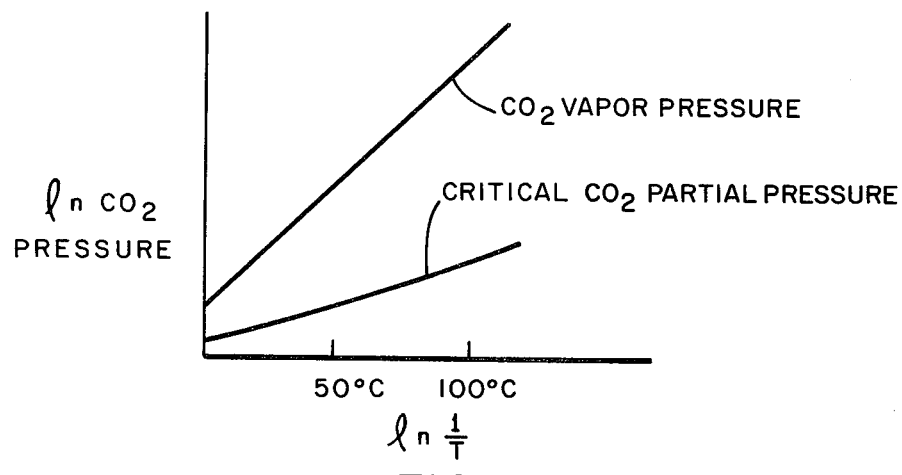
FIG. 2 is a chart showing the relationship of a membrane's critical carbon dioxide pressure with the carbon dioxide vapor pressure for various temperatures.

FIG. 2 is a graph showing carbon dioxide vapor pressure and critical carbon dioxide partial pressure plotted against temperature. Inasmuch as the amount of carbon dioxide which permeates the membrane is in direct proportion to the partial pressure of the carbon dioxide in contact with the membrane, it will readily be apparent from FIG. 2 that higher gas mixture temperatures can be used in order to get sufficiently high partial pressures to remove most of the carbon dioxide from the gas stream. This approach has the disadvantage that certain polymeric membranes cannot withstand higher temperatures. For example, a polysulfone membrane begins to deteriorate when exposed to temperatures of about 100° C. By the process of this invention, high percentages of such aggressive gases can be recovered from gas mixtures without running the risk of damaging or destroying the membrane of exposing it to high temperatures or high aggressive gas partial pressures.

Figure 4:
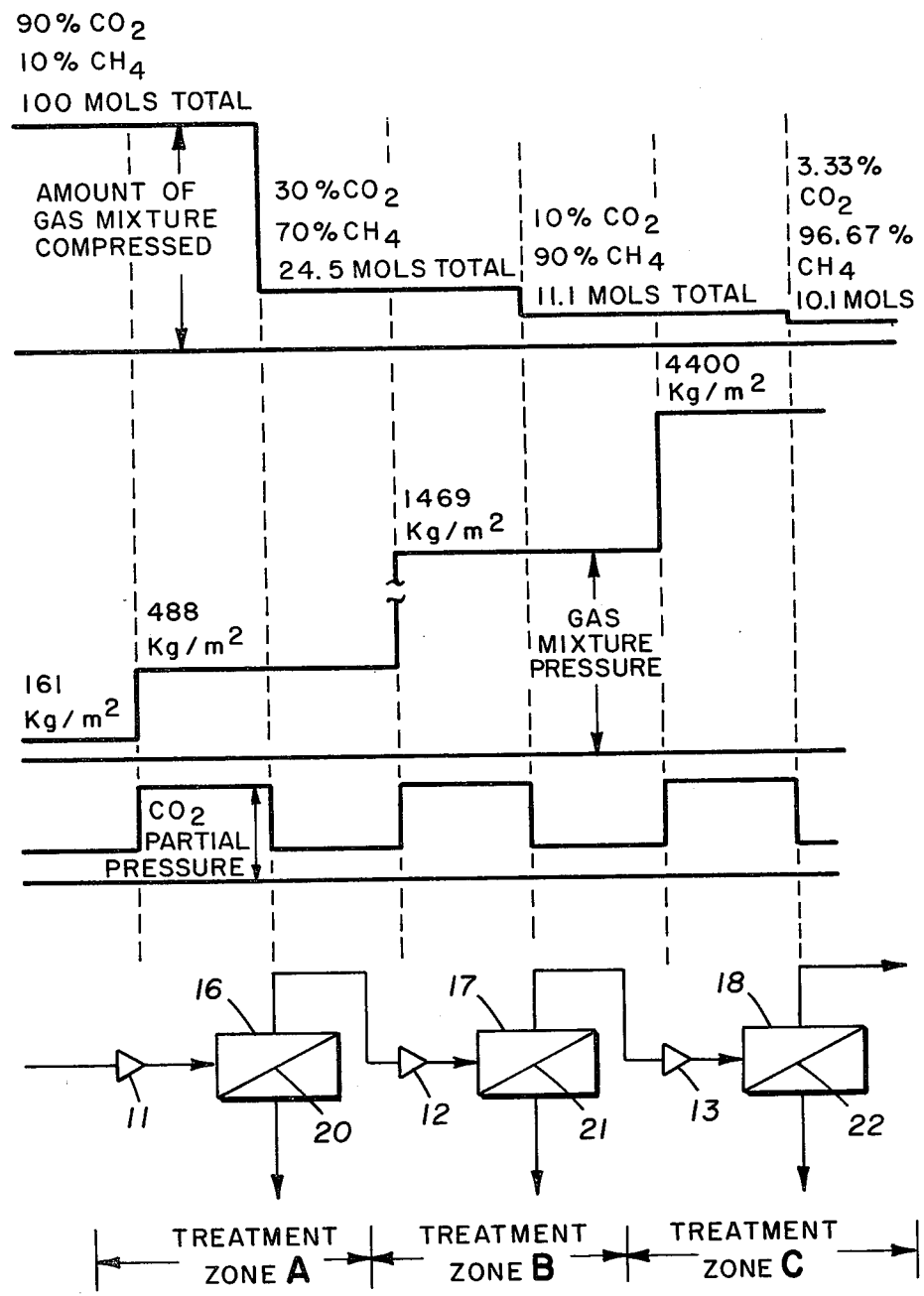
FIG. 4 shows the manner in which a high percentage of carbon dioxide can be separated from a gas mixture by the use of a membrane without resorting to high partial pressures.

FIG. 4 illustrates the manner in which the process of this invention is carried out. 100 moles of a mixture of 90 percent carbon dioxide and 10 percent methane is compressed in compressor 11 from a pressure of 161 Kg/m$^2$ to a pressure of 488 Kg/m$^2$ to thereby raise the partial pressure of the carbon dioxide in the mixture to a value of at least 75 percent of the critical carbon dioxide partial pressure. The compressed gas mixture is then brought into contact with the membrane 22, such as the polysulfone membrane disclosed in U.S. Pat. No. 4,230,463, in the separator 16 and maintained in contact with that membrane a length of time sufficient to allow enough of the carbon dioxide to pemeate the membrane to reduce the carbon dioxide partial pressure in the non-permeated gas mixture to less than 40 percent of the critical carbon dioxide pressure.

The compressed gas mixture is then passed through the compressor 12 in treatment zone B where it is compressed to a pressure of 1469 Kg/m$^2$, thereby again increasing the partial pressure of the carbon dioxide in the gas mixture to a value of at least 75 percent of the critical carbon dioxide partial pressure. The further compressed gas mixture is brought into contact with the membrane 21 in the separator 17 and is maintained in contact with that membrane a length of time sufficient to allow enough of the carbon dioxide to permeate the membrane that the partial pressure of the carbon dioxide in the non-permeated gas mixture is less than about 40 percent of the critical carbon dioxide partial pressure.

The gas mixture is then passed through the compressor 13 in the treatment zone C where it is compressed to a pressure of about 4400 Kg/m$^2$ to again increase the partial pressure of the carbon dioxide in the mixture to a value of at least 75 percent of the critical carbon dioxide pressure. The compressed gas mixture is brought into contact with the membrane 22 in the separator 18 to again lower the partial pressure of the carbon dioxide in the mixture. After leaving the separator 18, the gas mixture will contain less than about 20, preferably less than 5, percent carbon dioxide and will be at a pressure of at least three, preferably five, times the pressure of the gas mixture entering the compressor 11.

I claim:

1. A process for separating an aggressive gas from a mixture of said aggressive gas and at least one other gas, comprising
    (a) passing the gas mixture through a plurality of treatment zones connected in series,
    (b) in each zone first compressing the gas mixture,
    (c) then in each zone bringing the compressed gas mixture into contact with a feed side of a membrane having a critical partial pressure for the aggressive gas and being more permeable to the aggressive gas than said other gas such that the aggressive gas permeates the membrane to the other side thereof to thereby decrease the partial pressure of the aggressive gas on the feed side of the membrane, said gas mixture being compressed at a temperature and to such a pressure prior to contact with the membrane that the partial pressure of the aggressive gas is a least 75 percent of said critical partial pressure and the partial pressure of the aggressive gas is not above the critical partial pressure of the aggressive gas,
    (d) maintaining the gas mixture in contact with said feed side of said membrane a sufficient time to decrease the partial pressure of the aggressive gas on the feed side of the membrane to less than 40 percent of said critical partial pressure, and
    (e) passing the gas mixture through a sufficient number of treatment zones that the non-permeated gas mixture leaving the last treatment zone in said series contains less than 20 percent of said aggressive gas.

2. The process of claim 1 wherein the gas mixture is passed through at least three of said treatment zones.

3. The process of claim 1 wherein the pressure of the non-permeated gas leaving the last treatment zone in said series is at least three times the pressure of the gas mixture entering said first zone.

4. The process of claim 3 wherein the pressure of said non-permeated gas is at least five times the pressure of the gas mixture entering said first zone.

5. The process of claim 4 wherein said non-permeated gas contains less than 5 percent of said aggressive gas.

6. The process of claim 5 wherein the gas mixture is maintained in contact with the membrane for a sufficient time to decrease the partial pressure of the aggressive gas on the feed side of the membrane is less than 30 percent of said initial partial pressure.

7. The process of claim 5 wherein the aggressive gas is carbon dioxide.

8. The method of claim 7 wherein the membrane is made from a polysulfone polymer.

9. The process of claim 5 wherein said other gas is methane.

* * * * *